(12) United States Patent
Dehmel et al.

(10) Patent No.: US 7,212,737 B2
(45) Date of Patent: May 1, 2007

(54) VIDEOENDOSCOPIC SYSTEM

(75) Inventors: Joachim Dehmel, Hamburg (DE); Thomas Förster, Mölln (DE); Mathias Kraas, Haseldorf (DE); Gilbert Spahn, Schwarzenbek (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 311 days.

(21) Appl. No.: 11/058,674

(22) Filed: Feb. 15, 2005

(65) Prior Publication Data

US 2005/0191046 A1  Sep. 1, 2005

(30) Foreign Application Priority Data

Feb. 26, 2004  (DE) .................. 10 2004 009 384

(51) Int. Cl.
G03B 29/00 (2006.01)
H04N 7/18 (2006.01)
A61B 1/04 (2006.01)
A61B 1/07 (2006.01)

(52) U.S. Cl. .................. 396/17; 348/68; 348/73; 348/75; 600/172

(58) Field of Classification Search .................. 396/17, 396/267; 348/67, 68, 73, 75; 600/160, 172, 600/174, 175, 182
See application file for complete search history.

(56) References Cited

U.S. PATENT DOCUMENTS

| 4,884,133 A | * | 11/1989 | Kanno et al. .................. 348/68 |
| 4,905,082 A | | 2/1990 | Nishigaki et al. |
| 5,609,561 A | * | 3/1997 | Uehara et al. .............. 600/112 |
| 5,682,199 A | | 10/1997 | Lankford |
| 6,361,491 B1 | * | 3/2002 | Hasegawa et al. .......... 600/175 |
| 6,494,826 B1 | | 12/2002 | Chatenever et al. |
| 7,077,804 B2 | * | 7/2006 | Ota ............................. 600/180 |

* cited by examiner

Primary Examiner—W. B. Perkey
(74) Attorney, Agent, or Firm—Rankin, Hill, Porter & Clark LLP

(57) ABSTRACT

A videoendoscopic system (1) including an endoscope optical system (2) and a camera portion (3), the endoscope optical system (2) having an elongated shaft (4) through which an optical image guide (5) and a fiber light guide (6) pass, and an end housing (7), which is proximally connected to the shaft (4) and has an image exit window (10) and a light entry window (8) with radiation directions that are parallel to one another and to the axis of the shaft (4). The camera portion (3) includes a camera housing (15), from which an image signal cable (24) and a light guide cable (20) pass out, and an image entry window (18) and a light exit window (19), which are arranged with parallel radiation directions at a distance from the windows (8, 10) in the end housing (7) and the end housing (7). The camera housing (15) is constructed with a rotationally fixedly lockable coupling device (7, 16, 25, 26, 19) for coupling the windows (8, 19; 10, 18) to one another in a centering manner. The the coupling device has a cylinder (7) on one of the housings and a matching bore (16) on the other housing (15). The windows (8, 10; 19, 18) are arranged in the end wall (11) of the cylinder (7) and the base wall (17) of the bore (16).

11 Claims, 1 Drawing Sheet

VIDEOENDOSCOPIC SYSTEM

BACKGROUND OF THE INVENTION

1. Field of the Invention

The invention relates to a videoendoscopic system.

2. Description of Related Art

Such systems are disclosed in US 5,682,199 and US 6,494,826 B1. These prior systems both consist of an endoscope optical system and a camera housing which may be connected by means of a coupling, whereby both the image is coupled in one direction and the light is coupled in the other direction through the coupling point with appropriate windows. This manner of construction provides a series of advantages.

Of disadvantage with the known devices is the construction of the coupling with two parallel cylinders, which are arranged next to one another and fit into corresponding parallel bores in the opposing housing. The result of this is a complex housing structure with correspondingly large manufacturing costs and difficulties in handling.

SUMMARY OF THE INVENTION

The object of the present invention resides in simplifying a videoendoscopic system of the type referred to above as regards its structure and handling.

In accordance with the invention, the coupling has only a cylinder-bore engagement, whereby both the image beam path and also the light beam path pass through the cylinder with appropriate windows. The housing construction is thus considerably simplified and constructed in a manner which has greater functional clarity. The costs are thus reduced and handling becomes substantially more readily understandable and simpler. Considerable stability advantages are also produced by the increase in size, which is determined by the construction, of the diameter of the cylinder with respect to the cylinders of the known constructions. The coupling can be formed to have a precise guiding function and to be more highly loadable than in the known constructions with a simple type of construction.

The bore can be formed on one or other housing. It is, however, preferably formed on the camera housing, whereby advantages can be produced as regards space conditions in both housings.

The image window and light window can be arranged outside the axis of the cylinder. However, the image window preferably is advantageously arranged centrally with respect to the axis of the cylinder. Since the image window is situated in the axis of the shaft in the conventional construction, the cylinder is also situated concentrically with respect to the axis of the shaft. An overall central construction is thus produced with many structural advantages.

The windows can be disposed in the end surfaces of the cylinder and the bore respectively. If the surfaces are spaced apart, light reflections can propagate between the surfaces, which result in fogging from the light guide to the image window with consequent impairment of the image. The axial offset of the windows with respect to the position of the walls results in a position of the windows which is recessed in one of the walls so that a direct light path from the region between the light windows to the region between the image windows is blocked. A screening action is thus produced between the two window regions, whereby light fogging is prevented.

The camera can be fixedly arranged in the camera housing but is advantageously, rotatably, moveably arranged in it in order to enable the image to be positioned upright again by rotation of the camera, when the shaft is rotated, which necessarily also causes rotation of the camera housing due to the rotationally fixed coupling.

BRIEF DESCRIPTION OF THE DRAWINGS

The invention is illustrated schematically and by way of example in the single FIG. 1 in a partly sectional view of a videoendoscopic system in accordance with the invention.

DETAILED BRIEF DESCRIPTION OF THE INVENTION

Figure 1:
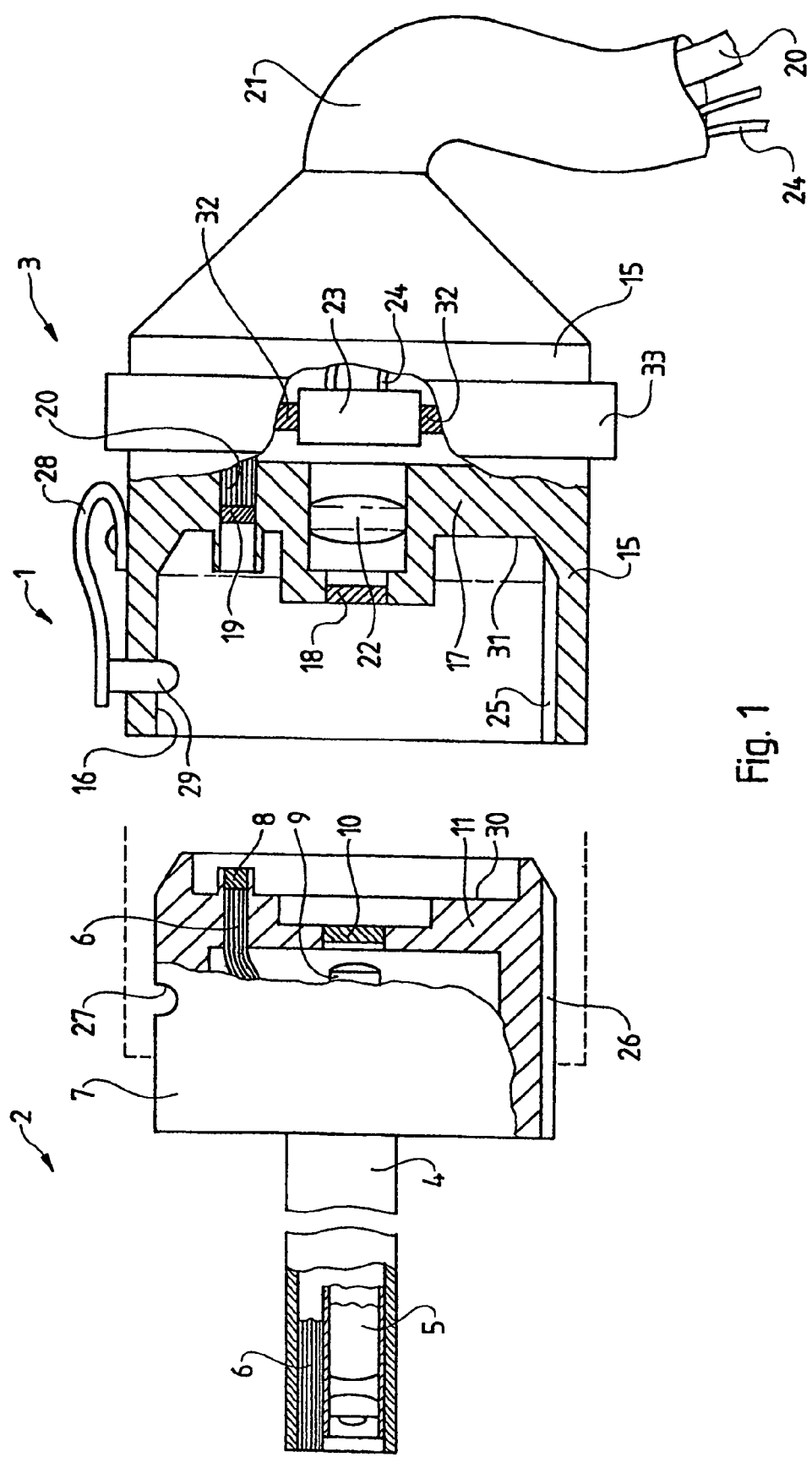

FIG. 1 shows a videoendoscopic system 1 consisting of an endoscope optical system 2 and a camera portion 3, which are constructed so that they may be coupled to one another. The endoscope optical system 2 has an elongate shaft 4, through which an optical image guide 5 passes, which is constructed in the exemplary embodiment in form of a relay lens system. Also passing through the shaft parallel to the optical image guide 5 is a fibre light guide 6, which radiates at the distal end of the shaft 4 parallel to the viewing direction.

At the proximal end of the shaft 4, the endoscope optical system 2 has an end housing 7, in which, as the partially sectioned view shows, the fibre light guide 6 terminates in front of a light entry window 8.

The optical image guide 5 terminates with a proximal end lens 9 in front of an image exit window 10.

The end housing 7 is constructed with a cylindrical peripheral shape with a cylinder axis, which passes centrally through the image exit window 10. The light entry window 8 is eccentrically arranged so that both windows 8, 10 are situated in the end wall 11 of the cylindrical end housing 7.

The camera portion 3 has a camera housing 15 with a bore 16 in its end surface, the internal diameter of which corresponds to the external diameter of the end housing 7. Disposed in the base wall 17 of the bore 16 is an image entry window 18 and a light exit window 19. A fibre light guide 20, which extends through the camera housing 15 and from it through an outlet cable 21, begins behind the light window 18. Situated behind the image entry window 18 is an objective 22 and the video camera 23, from which electric leads 24 extend to the exterior through the cable 21.

The windows 18, 19 are so arranged in the camera housing 15 that they are situated in alignment with the windows 10, 8 in the end housing 7, when the end housing 7 is inserted into the bore 16. Rotational alignment of the two housing 5, 7, 15 is necessary for this purpose due to the eccentric position of the light windows 8, 19. For this purpose, an inwardly projecting tongue 25, which fits into a corresponding groove 26 on the end housing 7, is provided in the bore 16 in the camera housing 15. Groove 26 and tongue 25 are arranged parallel to the axis.

Also provided on the end housing 7 is a transverse groove 27 and on the camera housing 15 there is a peg 29, which extends resiliently by virtue of a spring 28 through a hole transversely into the bore 16 and is intended for engagement in the transverse groove 27.

In an alternative embodiment, the end housing 7 and the bore 16 can also be of matching non-circular section which, however, requires a somewhat more complicated manufacturing process.

The outer surfaces 30 of the end wall 11 of the end housing 7 and 31 of the base wall 17 of the camera housing 15 are not situated, as may be seen in FIG. 1, in a plane with the associated windows 8, 10 and 19, 18, respectively. The windows are instead offset in the axial direction with respect to the surfaces 30 and 31, as may be seen in FIG. 1.

The image exit window 10 is offset distally in the axial direction with respect to the outer surface 30 whilst in this case the light entry window 8 is offset proximally. In the camera housing 15, the light exit window 19 is correspondingly offset proximally with respect to the surface 31 and the image entry window 18 is distally offset.

As shown in FIG. 1, even when, in the coupled position of the end housing 7 in the camera housing 15, the surfaces 30 and 31 are situated at a certain distance, a light path is produced between the pairs of windows 8, 19 and 10,18, which turns through a number of corners. Light exiting laterally between the light windows 8, 19 is thus prevented from passing into the image entry window 18 to the video camera 23.

As also shown in FIG. 1, the video camera 23 is coupled with devices 32 to a ring 33, which is rotationally mounted externally on the camera housing 15. By rotating the ring 33 with respect to the camera housing 15, the video camera 23 can be rotated with respect to the rotationally fixedly coupled housing 7, 15 and thus with respect to the shaft 4 in order to be able to produce an upright image orientation when the latter rotates during an operation.

The videoendoscopic system 1 is illustrated in FIG. 1 with an endoscope optical system 2 separate from the camera portion 3. For the purpose of coupling these two components, the end housing 7 is pushed into the bore 16 in the camera housing 15, whereby a rotary lock is provided by the tongue/groove engagement 25, 26 in one angular position, in which the light windows 8, 19 are in alignment. The spring loaded peg 29 locks in the transverse groove 27 and secures the coupled position.

Light passing from a light source, which is not shown, via the light guides 20 and 6 illuminates the field of the operation situated in front of the distal end of the shaft 4. The image picked up from there with the optical image guide 5 passes through the windows 10, 18 in the coupling point to the video camera 23 and from there via the leads 24 to an image evaluation and display device, which is not illustrated. If, whilst handling the device during an operation, the system is rotated, an upright image orientation can be produced again on the connected monitor by rotating the video camera 23 with the ring 33.

The invention claimed is:

1. A videoendoscopic system comprising an endoscope optical system and a camera portion, the endoscope optical system having an elongated shaft through which an optical image guide and a fiber light guide extend, and an end housing, which is proximally connected to the shaft and has an image exit window and a light entry window, the camera portion including a camera housing, extending from which are an image signal cable and a light guide cable, and an image entry window and a light exit window, the end housing and the camera housing carrying co-operating rotationally lockable coupling means arranged to couple the housings together and to lock the housing in a relative rotational position in which the image entry and exit windows are in alignment and the light entry and exit windows are in alignment, the coupling means including a cylinder with an end wall on one of the housings and a complementary bore with a base wall in the other housing, the windows being arranged in the end wall of the cylinder and the base wall of the bore.

2. The videoendoscopic system as claimed in claim 1, wherein the camera housing defines the bore.

3. The videoendoscopic system as claimed in claim 1, wherein the image entry and exit windows are situated on an axis of the cylinder.

4. The videoendoscopic system as claimed in claim 1, wherein the windows are arranged axially offset from an outer surface of the end wall and an outer surface the base wall, in which they are situated.

5. The videoendoscopic system as claimed in claim 1, wherein the camera is rotatably movably arranged within the camera housing.

6. The videoendoscopic system as claimed in claim 2, wherein the image entry and exit windows are situated on an axis of the cylinder.

7. The videoendoscopic system as claimed in claim 2, wherein the windows are arranged axially offset from an outer surface of the end wall and an outer surface the base wall, in which they are situated.

8. The videoendoscopic system as claimed in claim 3, wherein the windows are arranged axially offset from an outer surface of the end wall and an outer surface the base wall, in which they are situated.

9. The videoendoscopic system as claimed in claim 2, wherein the camera is rotatably movably arranged within the camera housing.

10. The videoendoscopic system as claimed in claim 3, wherein the camera is rotatably movably arranged within the camera housing.

11. The videoendoscopic system as claimed in claim 4, wherein the camera is rotatably movably arranged within the camera housing.

* * * * *